(12) United States Patent
Sakaida

(10) Patent No.: US 6,600,807 B2
(45) Date of Patent: Jul. 29, 2003

(54) METHOD OF AND APPARATUS FOR TAKING RADIATION IMAGES

(75) Inventor: Hideyuki Sakaida, Kaisei-machi (JP)

(73) Assignee: Fuji Photo Film Co., Ltd., Kanagawa-ken (JP)

(*) Notice: Subject to any disclaimer, the term of this patent is extended or adjusted under 35 U.S.C. 154(b) by 0 days.

(21) Appl. No.: 10/144,808

(22) Filed: May 15, 2002

(65) Prior Publication Data

US 2002/0176540 A1 Nov. 28, 2002

(30) Foreign Application Priority Data

May 16, 2001 (JP) .......................... 2001-146135

(51) Int. Cl.$^7$ ............................. G01N 23/04
(52) U.S. Cl. ........................... 378/62; 114/189
(58) Field of Search ................. 378/62, 114, 189

(56) References Cited

U.S. PATENT DOCUMENTS 6,404,848 B1 * 6/2002 Ishisaka et al. ............... 378/62
6,526,121 B1 * 2/2003 Hwu et al. ..................... 378/62

OTHER PUBLICATIONS

Peter Cloetens, et al., "Quantitative aspects of coherent hard X–ray imaging: Talbot images and holographic reconstruction." SPIE vol. 3154, pp. 72–82, 1997.

Peter Cloetens, et al., "Hard x–ray phase imaging using simple propagation of a coherent synchrotron radiation beam." J. Phys. D: Appl. Phys. 32, 1999, A145–A151.

* cited by examiner

*Primary Examiner*—Craig E. Church
(74) *Attorney, Agent, or Firm*—Sughrue Mion, PLLC

(57) ABSTRACT

A plurality of radiation images of an object is taken in different imaging positions. An area sensor which detects a radiation passing through the object is moved in a direction substantially parallel to the optical axis of the radiation. That the area sensor reaches one of the imaging positions is detected and the radiation is projected onto the area sensor only when the area sensor is in one of the imaging positions.

10 Claims, 8 Drawing Sheets

METHOD OF AND APPARATUS FOR TAKING RADIATION IMAGES

BACKGROUND OF THE INVENTION

1. Field of the Invention

This invention relates to a method of and an apparatus for taking a plurality of radiation images at different distances from the object which are suitable to generate a phase contrast image.

2. Description of the Related Art

There has been known a radiation image reproduction system in which an object is exposed to a radiation (X-rays, α-rays, β-rays, electron beams, ultraviolet rays or the like), the radiation passing through the object is detected by the use of, for instance, a stimulable phosphor sheet (to be described later) or a radiation detector panel (to be described later), thereby obtaining a radiation image data representing a radiation image of the object, and a radiation image is reproduced on the basis of the radiation image data after it is variously processed.

When certain kinds of phosphor are exposed to a radiation (X-rays, α-rays, β-rays, electron beams, ultraviolet rays), they store a part of energy of the radiation. Then when the phosphor which has been exposed to the radiation is exposed to stimulating rays such as visible light, light is emitted from the phosphor in proportion to the stored energy of the radiation. A phosphor exhibiting such properties is generally referred to as "a stimulable phosphor". In this specification, the light emitted from the stimulable phosphor upon stimulation thereof will be referred to as "stimulated emission". Further, a recording sheet comprising a layer of such a stimulable phosphor is referred to as "a stimulable phosphor sheet". When the stimulable phosphor sheet is used, the stimulable phosphor sheet is exposed to stimulating light after exposed to a radiation passing through an object and the stimulated emission emitted from the stimulable phosphor sheet upon exposure to the stimulating light is photo-electrically read, thereby obtaining image data representing a radiation image of the object. The radiation detector panel comprises a plurality of two-dimensionally arranged detecting elements and the detecting elements generates electric signals proportional to the amount of radiation projected onto the panel. Image data representing a radiation image of the object is obtained on the basis of the electric signals output from the detecting elements.

The radiation image thus obtained represents difference in intensity of the radiation passing through the object. For example, when the object includes a bone and a soft tissue, the radiation passing through the bone is largely attenuated and a very small part of the radiation reaches the detector (e.g., a stimulable phosphor sheet or a radiation detector panel) whereas the radiation passing through the soft tissue is less attenuated and a relatively large part of the radiation reaches the detector. Accordingly, in the case of such an object, the bone is expressed in white and the soft tissue is expressed in black. That is, a radiation image obtained is large in contrast and rich in information.

However, when the object mainly includes only soft tissues like a mammogram, difference in radiation attenuation by tissues is not so large, and accordingly, a radiation image obtained is small in contrast and poor in information.

In order to overcome this problem, there has been proposed a phase contrast imaging in which phase difference of radiation generated when the radiation passes through the object is visualized. The phase contrast imaging is based on the fact that when radiation is projected onto different materials, the phase of the wave of the radiation changes before and after passing through the materials and a phase difference is generated due to difference in propagation in the materials since radiation is an electromagnetic wave like light. When the object is of a soft part, a fine difference in tissues included in the soft part can be more clearly visualized by the phase contrast imaging since the phase difference is larger than the difference in attenuation. The phase contrast imaging is described in detail, for instance, in "Quantitative aspects of coherent hard X-ray imaging: Talbot images and holographic reconstruction" by Peter Cloetens, et al., (Proc, SPIE, Vol. 3154(1997), 72–82) (will be referred to as "paper 1", hereinbelow), and "Hard x-ray phase imaging using simple propagation of a coherent synchrotron radiation beam" by Peter Cloetens, et al., J. Phys. D:Appl. Phys.32(1999), A145–A151 (will be referred to as "paper 2", hereinbelow). According to these papers, a phase contrast image can be generated by taking images at a plurality of distances from the object by the use of a two-dimensional sensor (e.g., a radiation detector panel), thereby obtaining a plurality of pieces of image data representing a plurality of radiation images, and carrying out operation based on a predetermined algorithm by the use of the plurality of pieces of image data.

In the phase contrast imaging, it is necessary to obtain a plurality of radiation images by repeating process of taking a radiation image by exposing a two-dimensional sensor fixed to a predetermined position to radiation passing through an object and moving the two-dimensional sensor in parallel to the optical axis of the radiation to another position by the use of a sensor moving means, thereby obtaining a radiation image in each position.

However, the process of stopping the two-dimensional sensor in a plurality of positions and driving the radiation source in each of the positions is not a efficient way of obtaining a plurality of radiation images. It is possible to obtain a plurality of pieces of image data without stopping the two-dimensional sensor when image data representing a radiation image is read in time series. However, since in the two-dimensional sensor like a radiation detector panel, image data is obtained by reading out electric charges which are accumulated in the sensor in response to exposure to radiation, a certain response time is required between exposure of the sensor to the radiation and read out of the image data. Accordingly, an attempt of obtaining a plurality of pieces of image data without stopping the sensor encounters a problem that a radiation image in a certain position can overlap with that in the preceding position, which makes it difficult to obtain a precise radiation image in each position.

SUMMARY OF THE INVENTION

In view of the foregoing observations and description, the primary object of the present invention is to provide a method of and apparatus for efficiently and precisely obtaining a plurality of radiation images taken in different positions.

In accordance with a first aspect of the present invention, there is provided a method of obtaining a plurality of radiation images of an object taken in different imaging positions, wherein the improvement comprises the steps of moving an area sensor, which detects radiation passing through the object, in a direction substantially parallel to the optical axis of the radiation, detecting that the area sensor reaches one of the imaging positions, and projecting the radiation onto the area sensor only when the area sensor is in one of the imaging positions.

For example, the area sensor may be a radiation detector panel comprising a plurality of two-dimensionally arranged detecting elements.

The radiation images may be used to generate a phase contrast image.

In accordance with a second aspect of the present invention, there is provided an apparatus for obtaining a plurality of radiation images of an object taken in different imaging positions, wherein the improvement comprises an area sensor which detects radiation passing through the object, an area sensor moving means which moves the area sensor in a direction substantially parallel to the optical axis of the radiation, a switching means which performs switching between a projecting state, where the radiation is projected onto the object, and a non-projecting state, where the radiation is not projected onto the object, a position sensor which detects that the area sensor reaches one of the imaging positions, and a switching means control means which causes the switching means to switch from the non-projecting state to the projecting state when the position sensor detects that the area sensor is in one of the imaging positions.

The apparatus may further comprise a phase contrast image generating means which generates a phase contrast image on the basis of the radiation images taken in the different imaging positions.

The switching means may be a means which selectively drives or stops a radiation source which radiates the radiation or a shutter which is disposed on the optical axis of the radiation to selectively interrupt the radiation.

In the method and the apparatus of the present invention, radiation passing through an object is projected onto the area sensor only when the area sensor is one of the imaging positions, which permits to obtain a plurality of radiation images without stopping the area sensor in each imaging position. Further, since the radiation is not projected onto the area sensor when the area sensor is not in the imaging position, the problem that a radiation image in a certain position can overlap with that in the preceding position can be overcome, whereby a plurality of radiation images taken in different positions can be efficiently and precisely obtained.

DESCRIPTION OF THE PREFERRED EMBODIMENTS

Figure 1:
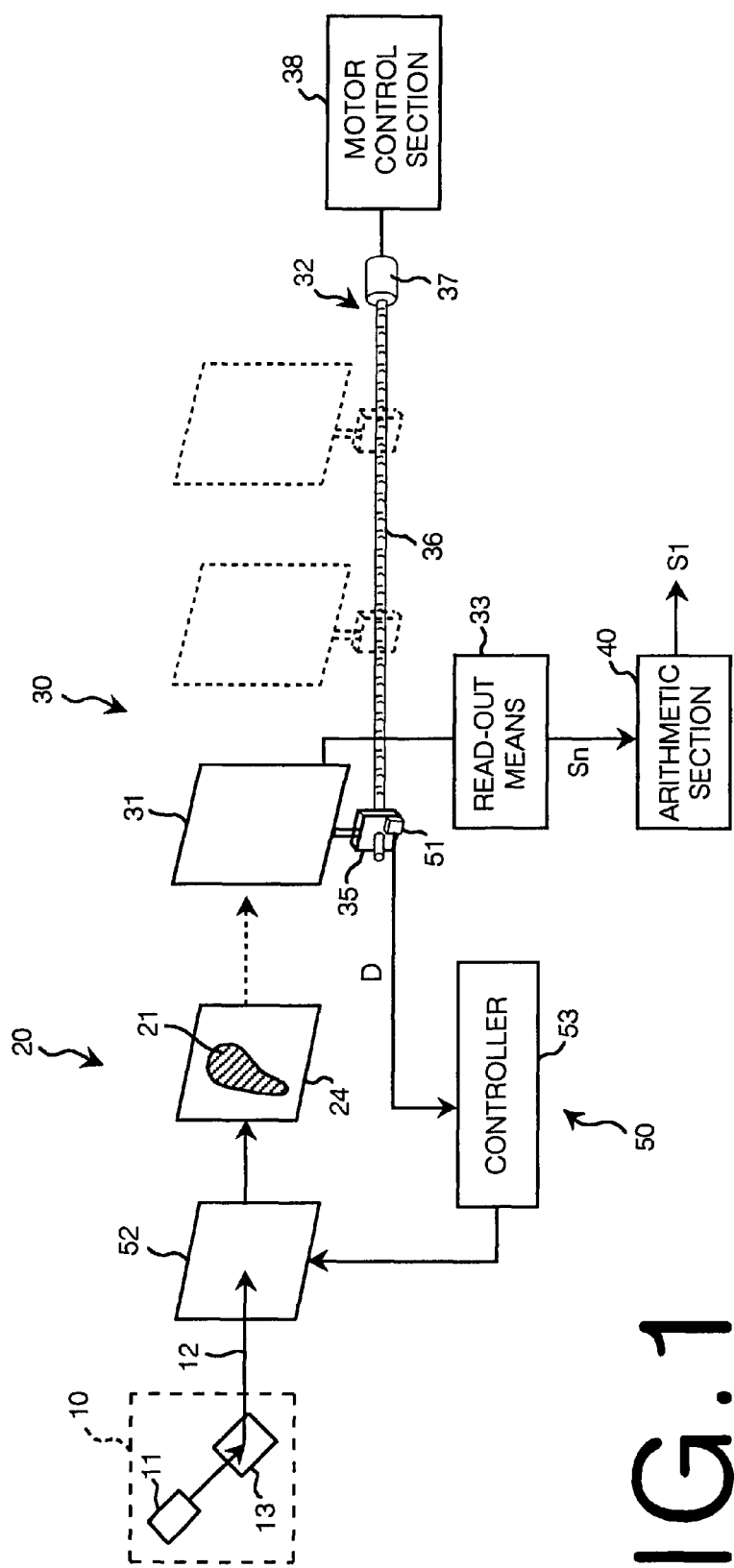
FIG. 1 is a schematic block diagram showing a phase contrast imaging apparatus in which a radiation image taking apparatus in accordance with a first embodiment of the present invention is employed.

In FIG. 1, a phase contrast imaging apparatus employing a radiation image taking apparatus in accordance with a first embodiment of the present invention comprises an X-ray source section 10 which radiates an X-ray, an object support section 20 which supports an object 21, a recording section 30 which detects the X-ray passing through the object 21 at different distances from the object 21 and obtains a plurality of pieces of image data Sn (n stands for 1 to N) representing a plurality of images of the object 21 taken at different distances, an arithmetic section 40 which obtains a phase contrast image data S1, representing a phase contrast image of the object 21, on the basis of the pieces of image data Sn, and a control section 50 which controls projection of X-ray onto the object 21.

The X-ray source section 10 comprises a source 11 which emits a synchrotron radiation and a crystal 13 which converts the synchrotron radiation into a monochromatic X-ray (will be simply referred to as "an X-ray"). The synchrotron radiation as emitted from the source 11 is reflected by the crystal 13 and turned into an X-ray 12.

The object support section 20 is provided with an support table 24 on which the object 21 is supported.

The recording section 30 comprises a detector panel 31 formed of a plurality of two-dimensionally arranged detecting elements, a panel moving means 32 which moves the detector panel 31 in a direction parallel to the direction of travel of the X-ray 12 passing through the object 21, and a read-out means 33 which reads out electric signals from the detecting elements of the detector panel 31 in a plurality of imaging positions set along the path of the detector panel 31 and obtains a piece of image data Sn in each of the imaging positions.

The panel moving means 32 comprises a support member 35 which is provided with a female thread and supports the detector panel 31, a threaded rod 36 which extends in a direction parallel to the direction of travel of the X-ray 12 and is provided with a male thread in mesh with the female thread of the support member 35, an electric motor 37 which rotates the threaded rod 36 about its rotating axis and a motor control section 38 which drives and stops the electric motor 37. As the motor 37 is driven by the motor control section 38, the threaded rod 36 is revolved and the detector panel 31 supported by the support member 35 is moved toward or away from the object 21 according to the direction of revolution of the threaded rod 36.

The arithmetic section 40 is provided with a memory (not shown) which temporarily stores a plurality of pieces of image data Sn and calculates image data S1 representing a phase contrast image on the basis of the pieces of image data Sn by a method described in the aforesaid paper 1. The method will be described, hereinbelow. It is assumed that the transmittance of the object is represented by the following formula (1).

$$T(x, y) = A(x, y) e^{i\psi(x, y)} \quad (1)$$

wherein T(x,y) represents a transmittance function, A(x,y) represents a transmittance intensity function, ψ(x,y) represents a phase shift function and (x,y) represents the coordinates representing the position on the detector panel 31.

When the object is a thin object whose transmittance intensity is negligible, that is, A(x,y) is substantially 1, the spatial frequency component of the phase shift is calculated by the use of the spatial frequency components $I_{dn}$(fx, fy) obtained by Fourier transform of images $I_{dn}$(x, y) taken at the distances dn (n=1 to N) between the object 21 and the detector panel 31 as represented by the following formula (2). In each of the images $I_{dn}$(x,y), the values of pixels are given by the values of pixels in the positions represented by (x,y) of the image data Sn taken at the distances dn.

$$\psi(fx, fy \neq 0) = \frac{\sum_{n=1\cdots N} \exp(i\pi\lambda dnf^2) Idn(fx, fy)}{N - \sum_{n=1\cdots N} \exp(2i\pi\lambda dnf^2)} \quad (2)$$

wherein N represents the number of pieces of image data Sn, f represents the spatial frequency, ψ(fx,fy≠0) represents the frequency component of the phase shift when the frequency is not 0, and Idn(fx,fy) represents the spatial frequency component of Idn(x,y).

By inverse Fourier transform of the spatial frequency component of the phase shift, the phase shift, i.e., the phase difference ψ(x,y) can be calculated. Since the phase difference ψ(x,y) takes a value in the range of from 0 to 2π, image data S1 representing the phase contrast image can be obtained by allocating the calculated phase difference ψ(x,y) to, for instance, values of 8 bits.

Though it is assumed here that the object is a thin object whose transmittance intensity is negligible, that is, A(x,y) is substantially 1, the phase shift can be calculated also for thick objects by the use of a similar algorithm.

The control section 50 comprises a position sensor 51 which is mounted on the support member 35 and outputs a detecting signal D when the detector panel 31 is brought to one of a plurality of predetermined imaging positions, a shutter 52 which is disposed on the optical path of the X-ray 12 between the X-ray source section 10 and the object support section 20, and the controller 53 which controls the shutter 52 on the basis of the detecting signal D output from the position sensor 51. The shutter 52 is of a metal such as lead impermeable to the X-ray 12.

Figure 2:
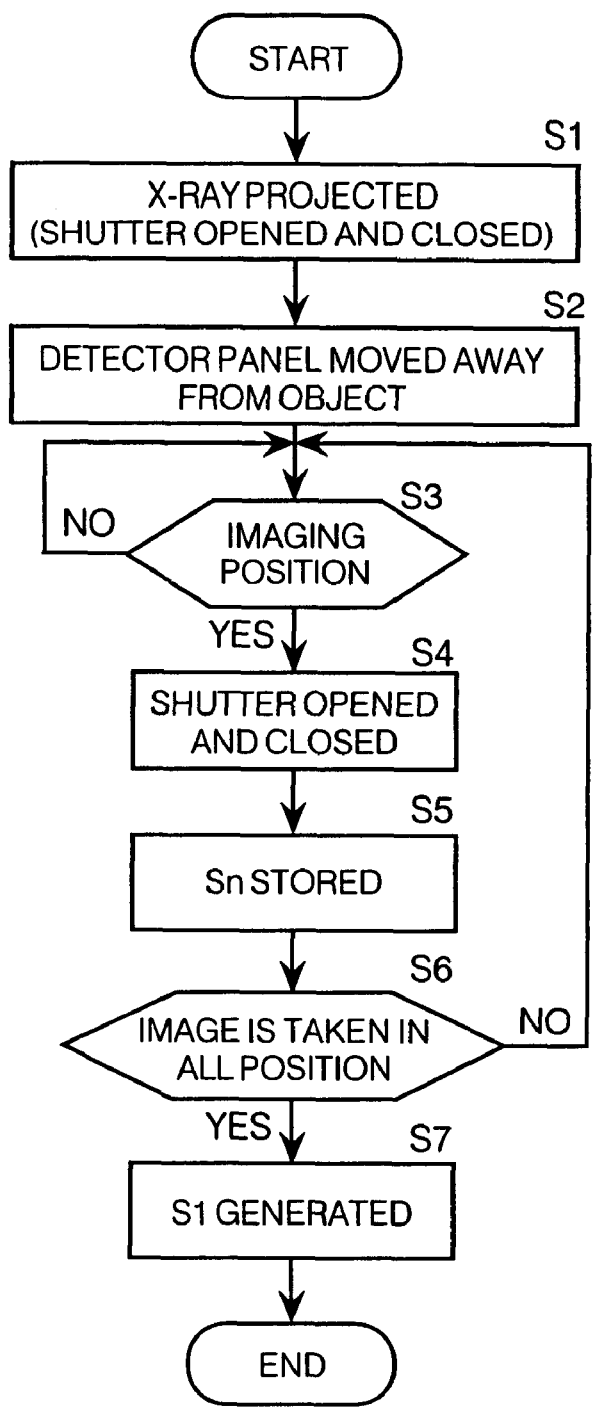
FIG. 2 is a flow chart for illustrating the operation of the radiation image taking apparatus of the first embodiment.

The operation of the phase contrast imaging apparatus employing the radiation image taking apparatus in accordance with the first embodiment of the present invention will be described, hereinbelow, with reference to the flow chart shown in FIG. 2. The source 11 is driven to emit a synchrotron radiation and the synchrotron radiation is reflected by the crystal 13 and is converted into a monochromatic X-ray 12. Then the shutter 52 is once opened and closed so that the X-ray 12 is projected onto the object 21 while the shutter 52 is opened. (step S1) Then the control section 38 drives the motor 37 to move the detector panel 31 away from the object 21. (step S2) When the detector panel 31 reaches an imaging position, the controller 53 opens and closes the shutter 52 so that the X-ray 12 passing through the object 21 is projected onto the detector panel 31 in the imaging position. (steps S3 and S4) A radiation image of the object 21 in the imaging position recorded on the detector panel 31 as electric charges of the detecting elements of the detector panel 31 is read out by the read-out means 33 and image data Sn representing the radiation image is stored in the memory of the arithmetic section 40. (step S5) After the radiation images are taken in all the imaging positions, the arithmetic section 40 generates phase contrast image data S1 on the basis of a plurality of pieces of image data Sn stored in the memory of the arithmetic section 40, according to the aforesaid formula (2). (steps S6 and S7) An image based on the phase contrast image data is reproduced on a monitor or output as a print.

As can be understood from the description above, X-ray 12 passing through the object 21 is projected onto the detector panel 31 only when the detector panel 31 is in an imaging position, and accordingly, a plurality of pieces of image data Sn representing radiation images of the object 21 in different imaging positions can be obtained without stopping the detector panel 31. Further, the problem that a radiation image in a certain position can overlap with that in the preceding position, which is involved when the detector panel 31 is continuously exposed to the X-ray 12, can be overcome, whereby a plurality of pieces of image data Sn representing radiation images of the object 21 in different imaging positions can be efficiently and precisely obtained.

Figure 3:
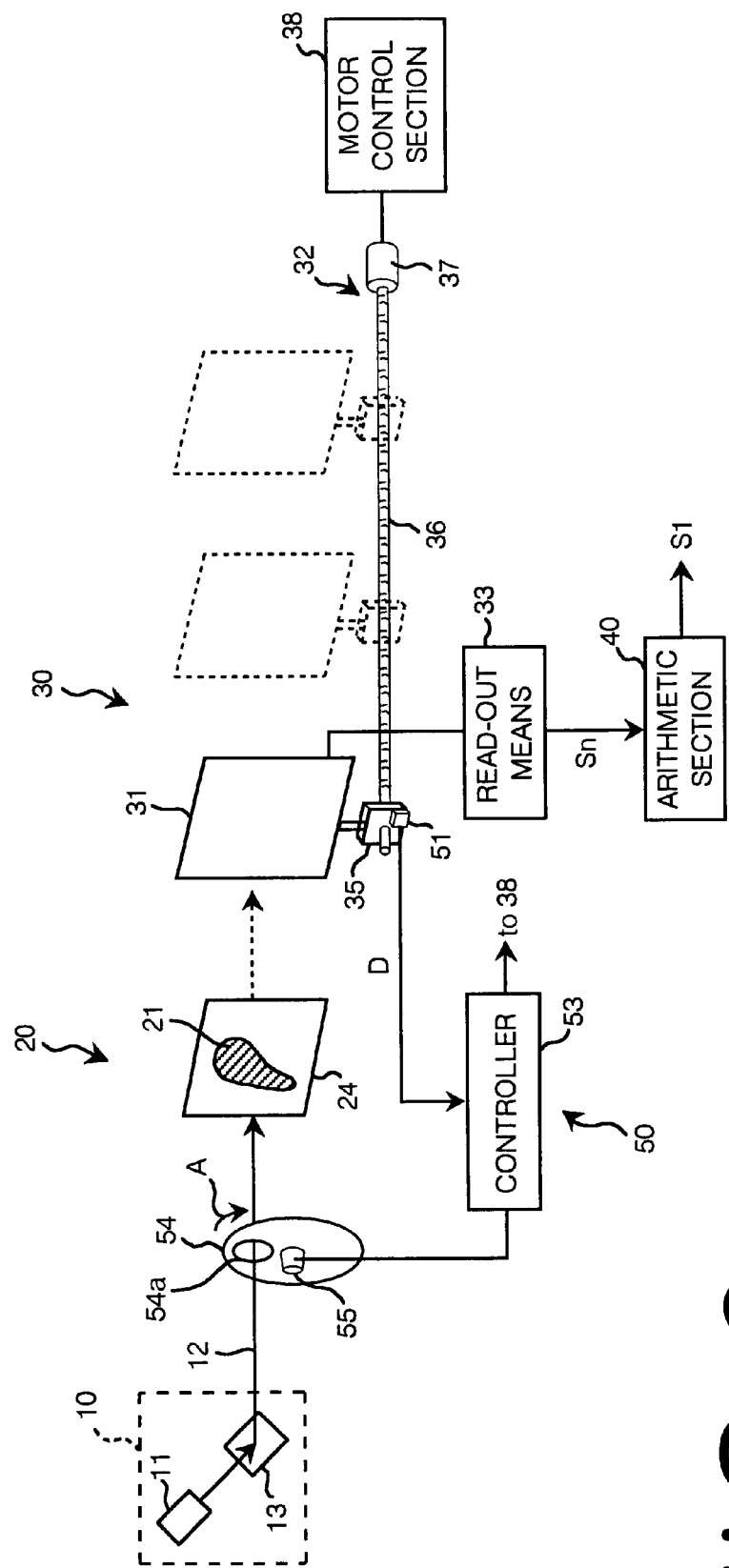
FIG. 3 is a schematic block diagram showing a phase contrast imaging apparatus in which a radiation image taking apparatus in accordance with a second embodiment of the present invention is employed.
Figure 4:
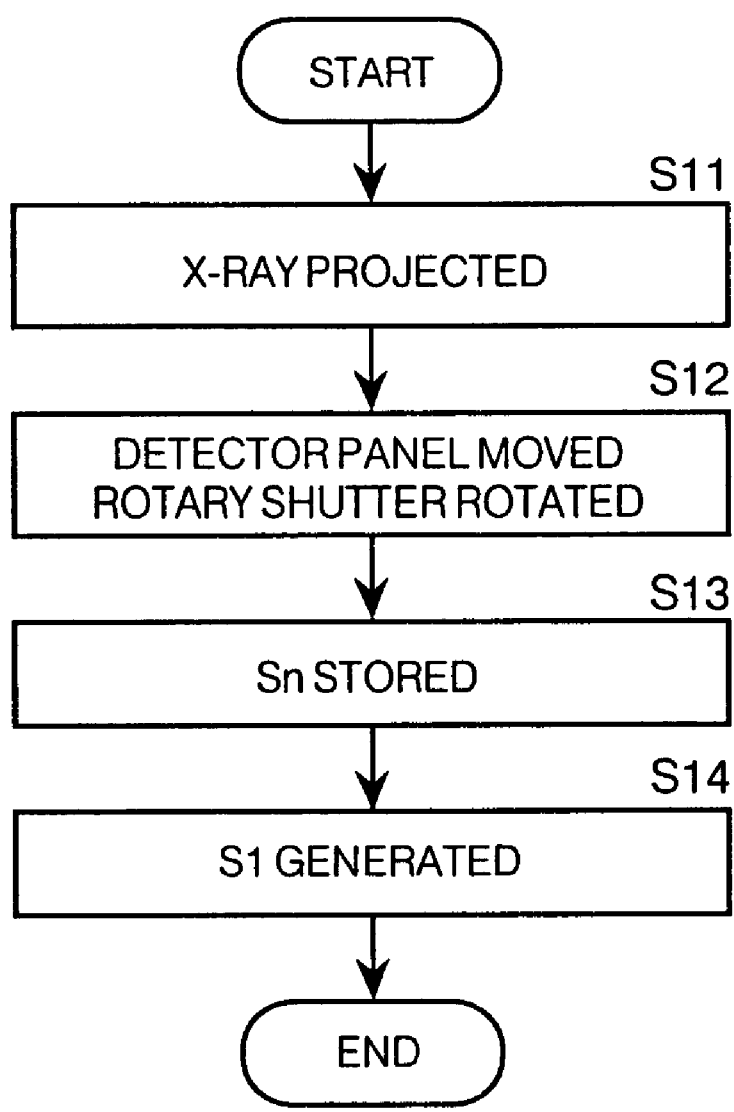
FIG. 4 is a flow chart for illustrating the operation of the radiation image taking apparatus of the second embodiment.

A phase contrast imaging apparatus in which a radiation image taking apparatus in accordance with a second embodiment of the present invention is employed will be described with reference to FIGS. 3 and 4, hereinbelow. In FIG. 3, the elements analogous to those shown in FIG. 1 are given the same reference numerals and will not be described here. The phase contrast imaging apparatus shown in FIG. 3 differs from that shown in FIG. 1 in that a rotary shutter 54 provided with a circular window 54a permeable to the X-ray 12 and rotated in the direction of arrow A by a motor 55 is employed in place of the shutter 52. The controller 53 controls the motor control section 38 and the motor 55 so that the moving speed of the detector panel 31 and the rotating speed of the rotary shutter 54 are synchronized with each other in such a manner that the window 54a of the rotary shutter 54 is positioned on the optical path of the X-ray 12 just when the detector panel 31 is in an imaging position.

It is assumed here that the optical axis of the X-ray 12 extends along z-axis, the initial position of the detector panel 31 is a position where z=0, and the center of the window 54a of the rotary shutter 54 is on the optical path of the X-ray 12 when the rotating angle θ of the window 54a is 0. When the rotary shutter 54 is started to rotate at an angular speed of ω with the detector panel 31 started to move at a speed of v at time t, a radiation image of the object 21 is taken each time the rotating angle θ (t) (=ωt) becomes equal to 2kπ (k is an integer), that is, each time the value of z representing the position of the detector panel 31 becomes equal to 2kπ v/ω. Accordingly, the controller 53 controls the motor control section 38 and the motor 55 to control the moving speed v of the detector panel 31 and the angular speed ω of the rotary shutter 54 so that θ (t)=2kπ is satisfied each time a detecting signal D is input from the position sensor 51.

The operation of the phase contrast imaging apparatus employing the radiation image taking apparatus in accordance with the second embodiment of the present invention will be described, hereinbelow, with reference to the flow chart shown in FIG. 4. The source 11 is driven to emit a synchrotron radiation and the synchrotron radiation is reflected by the crystal 13 and is converted into a monochromatic X-ray 12. Thus the X-ray 12 is projected onto the object 21. (step S11) Then the controller 53 controls the control section 38 and the motor 55 to drive the motor 37 to move the detector panel 31 away from the object 21 and to rotate the rotary shutter 54. (step S12) Rotation of the rotary shutter 54 and movement of the detector panel 31 are synchronized with each other so that the center of the window 54a of the rotary shutter 54 is brought to the optical path of the X-ray 12 and the X-ray 12 passing through the object 21 is projected onto the detector panel 31 through the window 54a each time the detector panel 31 reaches an imaging position. A radiation image of the object 21 in the imaging position recorded on the detector panel 31 as electric charges of the detecting elements of the detector panel 31 is read out by the read-out means 33 and image data Sn representing the radiation image is stored in the memory of the arithmetic section 40. (step S13) After the radiation images are taken in all the imaging positions, the arithmetic section 40 generates phase contrast image data S1 on the basis of a plurality of pieces of image data Sn stored in the memory of the arithmetic section 40, according to the aforesaid formula (2). (step S14)

Figure 5:
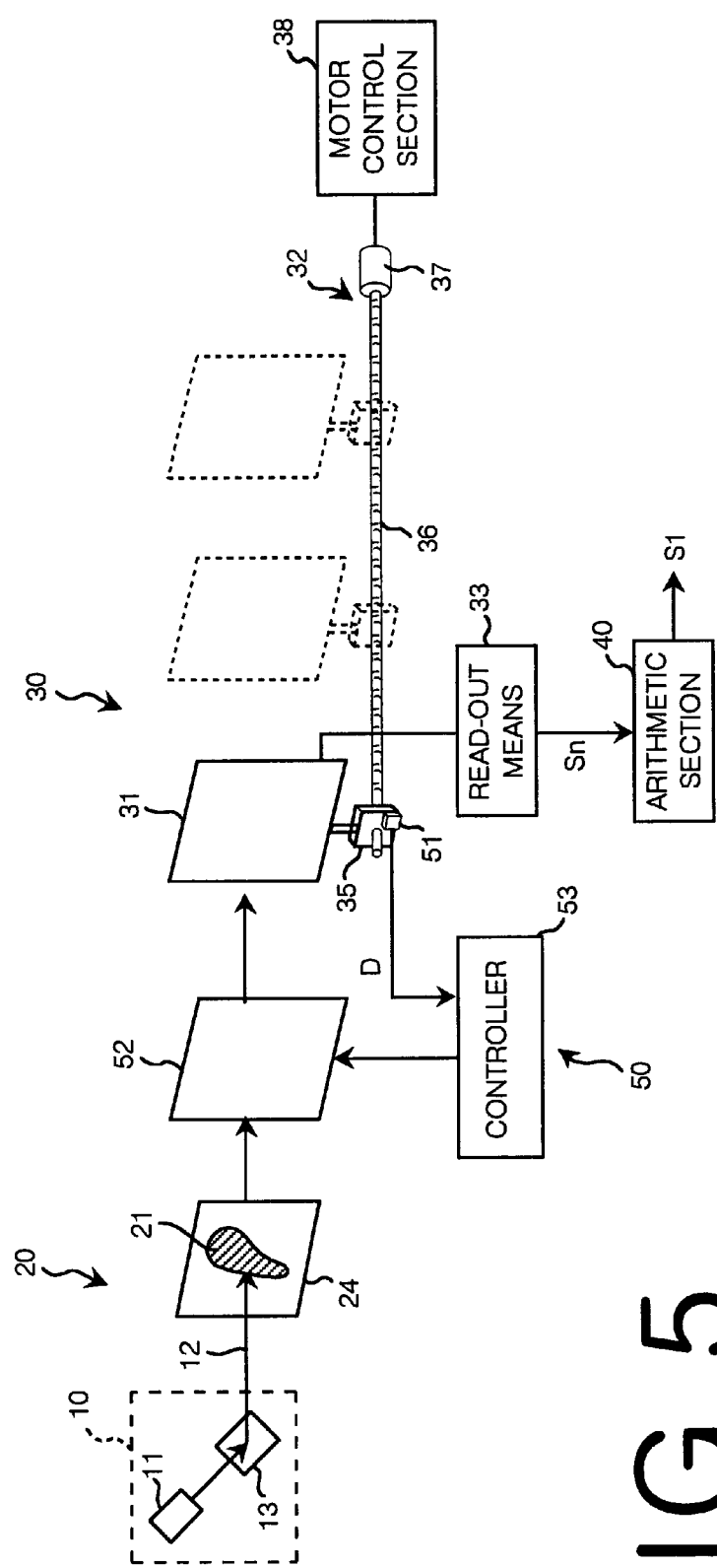
FIG. 5 is a schematic block diagram showing a phase contrast imaging apparatus in which a radiation image taking apparatus in accordance with a third embodiment of the present invention is employed.

Though, in the first second embodiment, the shutter 52 is disposed between the X-ray source section 10 and the object support section 30, the shutter 52 may be disposed between the object support section 20 and the recording section 30 as in a third embodiment shown in FIG. 5. Similarly, though the rotary shutter 54 may be disposed between the object support section 20 and the recording section 30.

Figure 6:
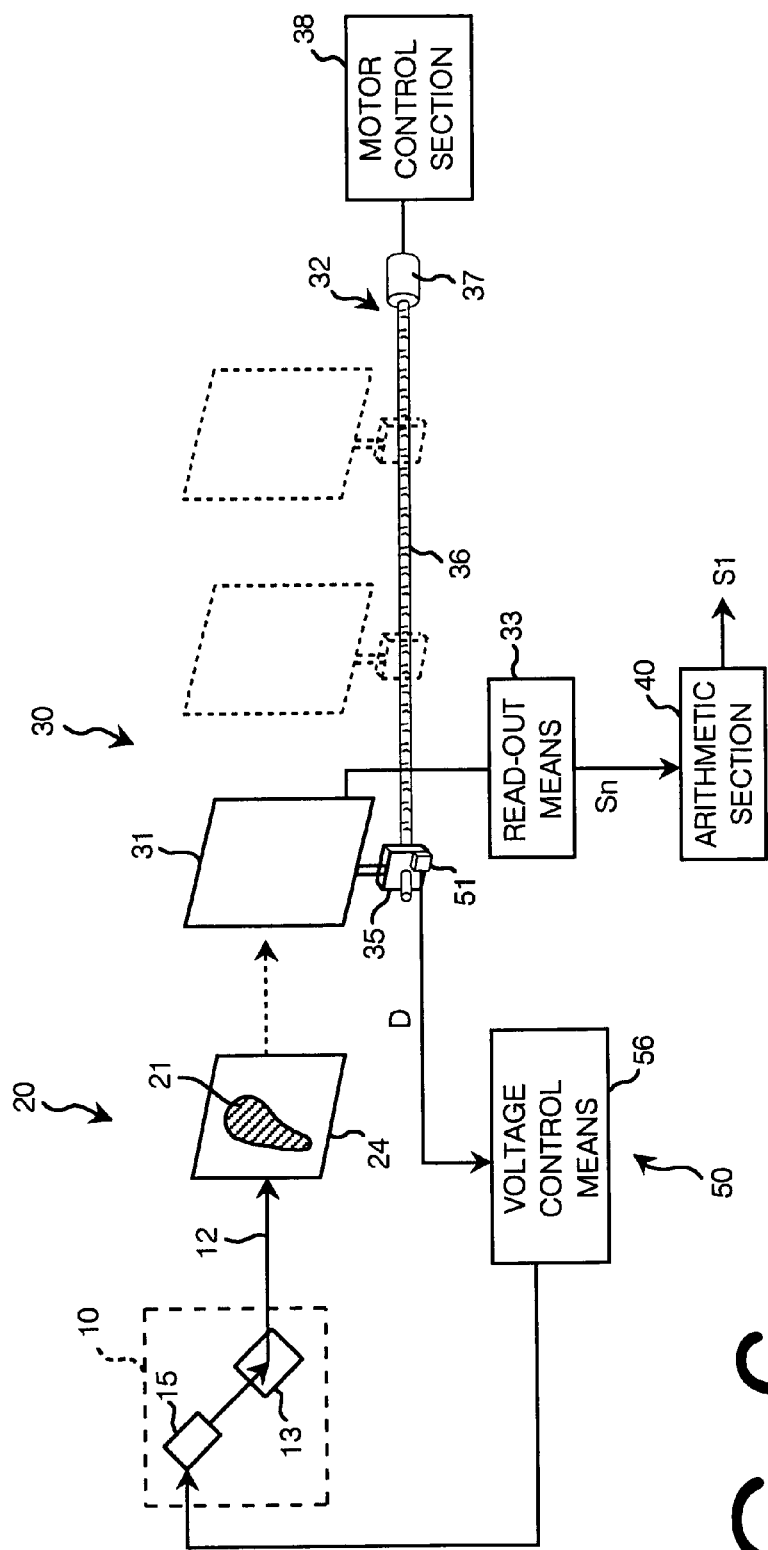
FIG. 6 is a schematic block diagram showing a phase contrast imaging apparatus in which a radiation image taking apparatus in accordance with a fourth embodiment of the present invention is employed.
Figure 7:
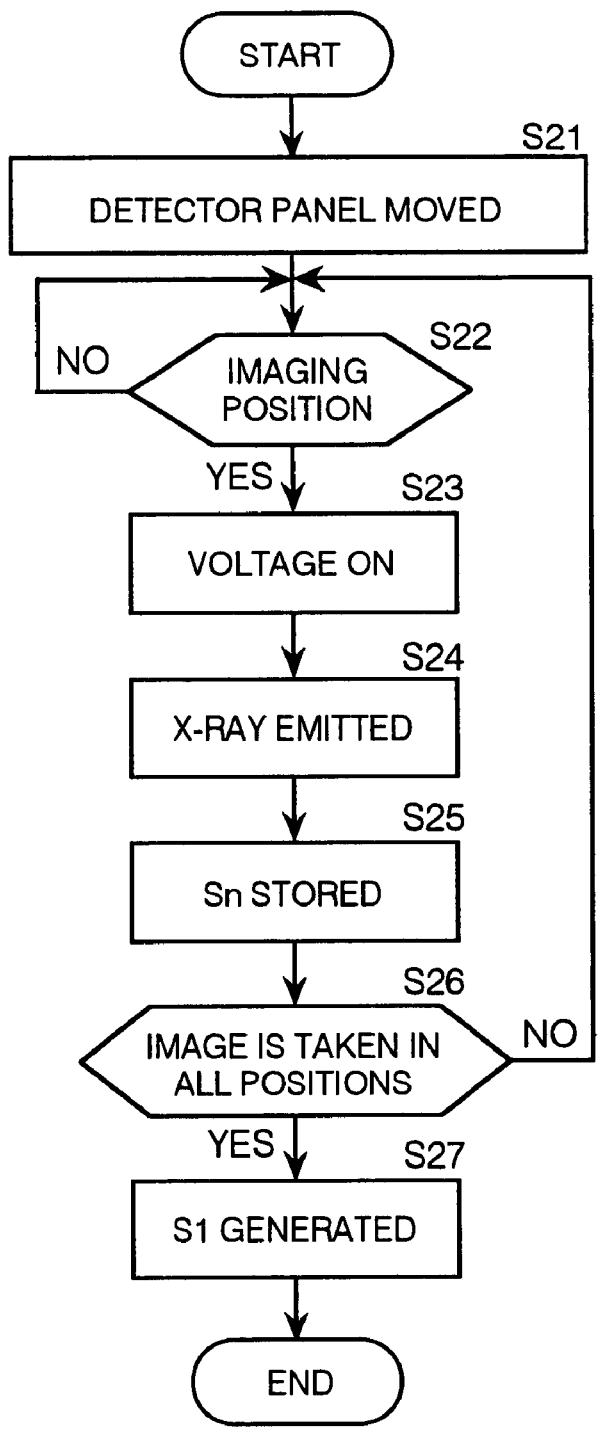
FIG. 7 is a flow chart for illustrating the operation of the radiation image taking apparatus of the fourth embodiment.

A phase contrast imaging apparatus in which a radiation image taking apparatus in accordance with a fourth embodiment of the present invention is employed will be described with reference to FIGS. 6 and 7, hereinbelow. In FIG. 6, the elements analogous to those shown in FIG. 1 are given the same reference numerals and will not be described here. The phase contrast imaging apparatus shown in FIG. 6 differs from that shown in FIG. 1 in that a micro focus X-ray tube 15 is employed as the source 11, and a voltage control means 56 which turns on and off the micro focus X-ray tube 15 according to the detecting signal D is employed in place of the shutter 52 and the controller 53.

The operation of the phase contrast imaging apparatus employing the radiation image taking apparatus in accordance with the fourth embodiment of the present invention will be described, hereinbelow, with reference to the flow chart shown in FIG. 7. The control section 38 drives the motor 37 to move the detector panel 31 away from the object 21. (step S21) When the detector panel 31 reaches an imaging position, the voltage control means 56 turns on the voltage applied to the micro focus X-ray tube 15 and the X-ray 12 is emitted from the tube 15. Then the X-ray 12 passing through the object 21 is projected onto the detector panel 31 in the imaging position. (steps S22 to S24) A radiation image of the object 21 in the imaging position recorded on the detector panel 31 as electric charges of the detecting elements of the detector panel 31 is read out by the read-out means 33 and image data Sn representing the radiation image is stored in the memory of the arithmetic section 40. (step S25) After the radiation images are taken in all the imaging positions, the arithmetic section 40 generates phase contrast image data S1 on the basis of a plurality of pieces of image data Sn stored in the memory of the arithmetic section 40, according to the aforesaid formula (2). (steps S26 and S27)

Figure 8:
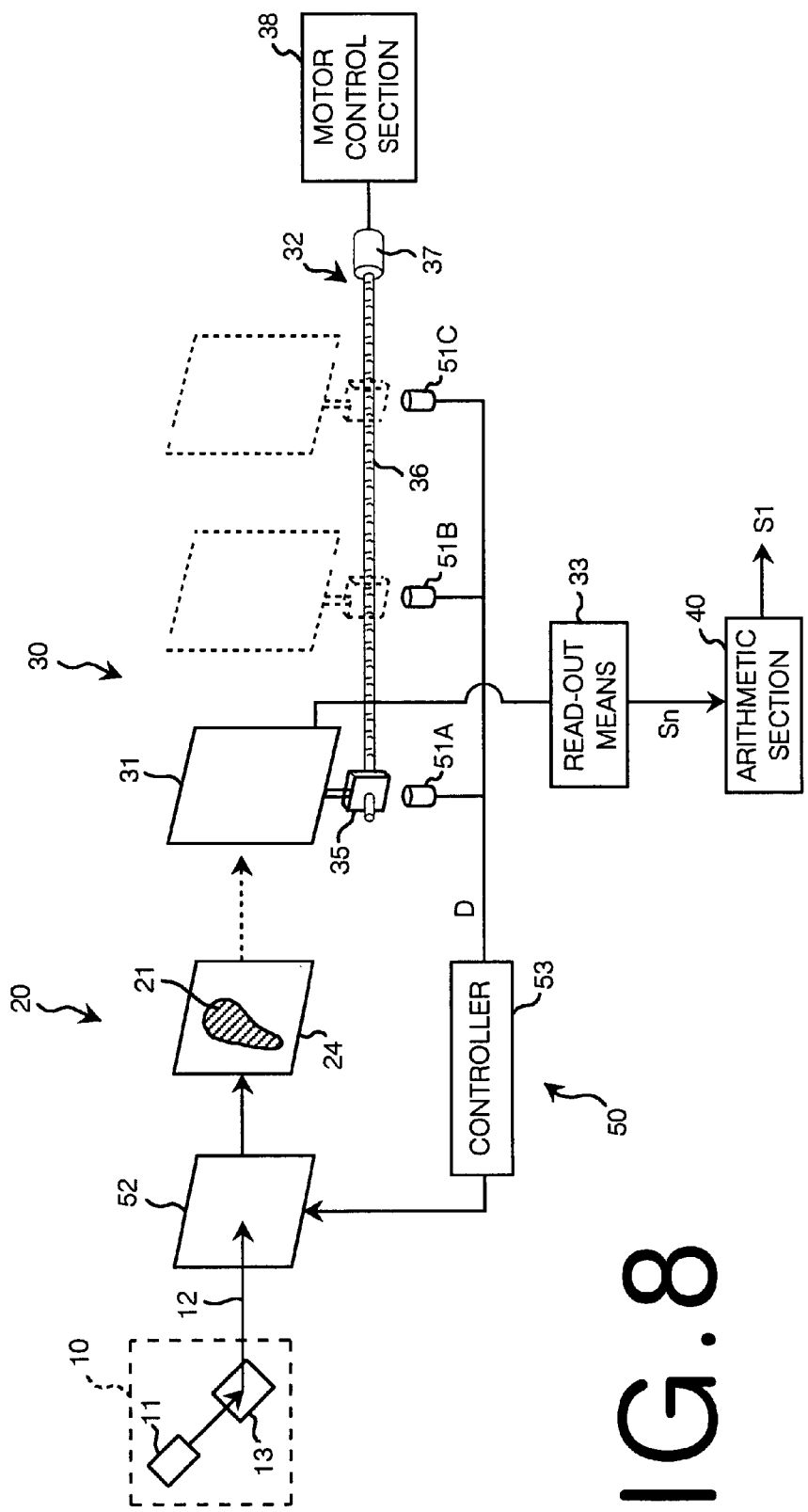
FIG. 8 is a schematic block diagram showing a phase contrast imaging apparatus in which a radiation image taking apparatus in accordance with a fifth embodiment of the present invention is employed.

Though, in the first to fourth embodiments, that the detector panel 31 reaches an imaging position is detected by the position sensor 51 carried by the support member 35, it is possible to dispose three position sensors 51A, 51B and 51C respectively in a plurality of (three in these particular embodiments) imaging positions so that that the detector panel 31 reaches each of the imaging positions is detected by each of the position sensors 51A to 51C as shown in FIG. 8.

Though, in the embodiments described above, the panel moving means 32 comprises the support member 35, the threaded rod 36, the electric motor 37 and the motor control section 38, the panel moving means 32 may be of any structure so long as it can move the detector panel 31 in a direction parallel to the optical axis of the X-ray 12. For example, the support member 35 may be mounted on a rail extending in a direction parallel to the optical axis of the X-ray 12 to be movable along the rail.

Further, the source of the X-ray 12 need not be limited to those emitting a synchrotron radiation. The X-ray 12 need not be limited to a monochromatic X-ray.

Further, though, in the embodiments described above, an X-ray is employed as the radiation, a radiation other than X-ray, e.g., α-ray, β-ray, γ-ray, an electron beam or an ultraviolet ray, may be employed.

A computer program for causing a computer to perform the method of the present invention may be recorded in a computer readable medium so that the computer can perform the method when loaded with the recording medium. A skilled artisan would know that the computer readable medium is not limited to any specific type of storage devices and includes any kind of device, including but not limited to CDs, floppy disks, RAMs, ROMs, hard disks, magnetic tapes and internet downloads, in which computer instructions can be stored and/or transmitted. Transmission of the computer code through a network or through wireless transmission means is also within the scope of this invention. Additionally, computer code/instructions include, but are not limited to, source, object and executable code and can be in any language including higher level languages, assembly language and machine language.

What is claimed is:

1. A method of obtaining a plurality of radiation images of an object taken in different imaging positions, wherein the improvement comprises the steps of moving an area sensor, which detects a radiation passing through the object, in a direction substantially parallel to the optical axis of the radiation, detecting that the area sensor reaches one of the imaging positions, and projecting the radiation onto the area sensor only when the area sensor is in one of the imaging positions.

2. A method as defined in claim 1 in which the radiation images are used to generate a phase contrast image.

3. An apparatus for obtaining a plurality of radiation images of an object taken in different imaging positions, wherein the improvement comprises an area sensor which detects a radiation passing through the object, an area sensor moving means which moves the area sensor in a direction substantially parallel to the optical axis of the radiation, a switching means which performs switching between a projecting state, where the radiation is projected onto the object, and a non-projecting state, where the radiation is not projected onto the object, a position sensor which detects that the area sensor reaches one of the imaging positions, and a switching means control means which causes the switching means to switch from the non-projecting state to the projecting state when the position sensor detects that the area sensor is in one of the imaging positions.

4. An apparatus as defined in claim 3 further comprising a phase contrast image generating means which generates a phase contrast image on the basis of the radiation images taken in the different imaging positions.

5. An apparatus as defined in claim 3 in which the switching means is a means which selectively drives or stops a radiation source which radiates the radiation.

6. An apparatus as defined in claim 3 in which the switching means is a shutter which is disposed on the optical axis of the radiation to selectively interrupt the radiation.

7. A computer program for causing a computer to perform a procedure comprising the steps of moving an area sensor, which detects a radiation passing through the object, in a direction substantially parallel to the optical axis of the radiation, detecting that the area sensor reaches one of the imaging positions, and projecting the radiation onto the area sensor only when the area sensor is in one of the imaging positions, thereby obtaining a plurality of radiation images of an object taken in different imaging positions.

8. A computer program as defined in claim 7 in which the procedure further comprises a step of generating a phase contrast image on the basis of the radiation images.

9. A computer readable medium in which is recorded computer program for causing a computer to perform a procedure comprising the steps of moving an area sensor, which detects a radiation passing through the object, in a direction substantially parallel to the optical axis of the radiation, detecting that the area sensor reaches one of the imaging positions, and projecting the radiation onto the area sensor only when the area sensor is in one of the imaging positions, thereby obtaining a plurality of radiation images of an object taken in different imaging positions.

10. A computer readable medium as defined in claim 9 in which the procedure further comprises a step of generating a phase contrast image on the basis of the radiation images.

* * * * *